(12) United States Patent
Mori et al.

(10) Patent No.: US 8,252,273 B2
(45) Date of Patent: Aug. 28, 2012

(54) ULTRAVIOLET ABSORBER

(75) Inventors: Masao Mori, Toyama (JP); Haruo Saito, Toyama (JP)

(73) Assignee: Lead Chemical Co., Ltd., Toyama (JP)

( * ) Notice: Subject to any disclaimer, the term of this patent is extended or adjusted under 35 U.S.C. 154(b) by 0 days.

(21) Appl. No.: 12/677,900

(22) PCT Filed: Apr. 2, 2008

(86) PCT No.: PCT/JP2008/056589
§ 371 (c)(1), (2), (4) Date: Mar. 12, 2010

(87) PCT Pub. No.: WO2009/041098
PCT Pub. Date: Apr. 2, 2009

(65) Prior Publication Data
US 2010/0239508 A1      Sep. 23, 2010

(30) Foreign Application Priority Data
Sep. 27, 2007  (WO) ................. PCT/JP2007/068836

(51) Int. Cl.
*A61K 8/49*     (2006.01)
*A61K 8/00*     (2006.01)
*C07C 69/76*    (2006.01)

(52) U.S. Cl. ........ 424/70.9; 424/60; 424/70.8; 424/401; 560/8

(58) Field of Classification Search .................. None
See application file for complete search history.

(56) References Cited

U.S. PATENT DOCUMENTS
| | | | |
|---|---|---|---|
| 2005/0272139 A1 | 12/2005 | Venkateswaran et al. | |
| 2006/0051303 A1 | 3/2006 | Mori et al. | |

FOREIGN PATENT DOCUMENTS
| | | | |
|---|---|---|---|
| JP | 03297685 | * | 12/1991 |
| JP | A-3-297685 | | 12/1991 |
| JP | A-7-26247 | | 1/1995 |
| JP | A-2001-49233 | | 2/2001 |
| JP | A-2004-51567 | | 2/2004 |
| JP | A-2004-175778 | | 6/2004 |
| WO | WO 2004/041771 A1 | | 5/2004 |

OTHER PUBLICATIONS

2-Propenoic acid, 3-(4-propoxyphenyl)-, 2-methyphenylester: STN Registry file- entered on Jun. 27, 2007.*
2-propenoic acid, 3-(4-methoxyphenyl)-, 2-methylphenyl ester. Entered Jun. 17, 2002. Accessed Mar. 16, 2011.*
2-propenoic acid, 3-(4-ethoxyphenyl)-, 2-methylphenyl ester. Entered Jun. 17, 2002. Accessed Mar. 16, 2011.*
Jun. 24, 2008 Search Report issued in PCT/JP2008/056589.
"2-Propenoic acid, 3-(4-butoxyphenyl)-, 2-methylphenl ester" CHEMCATS, Oct. 24, 2002, XP007914861.
"2-Propenoic acid, 3-(4-propoxyphenyl)-, 2-methylphen1 ester" CHEMCATS, Jun. 27, 2007, XP007914860.

* cited by examiner

*Primary Examiner* — David J Blanchard
*Assistant Examiner* — Lori K Mattison
(74) *Attorney, Agent, or Firm* — Oliff & Berridge, PLC

(57) ABSTRACT

There is provided an ultraviolet absorber having a strong absorptive capacity in the UVA range and an absorptive capacity in the UVB range to have an ultraviolet inhibitory effect in a wide range of wavelength, increasing in an ultraviolet absorptive capacity over the course of ultraviolet irradiation time in both the UVA and the UVB ranges and having an excellent solubility. An ultraviolet absorber comprising, as an active ingredient, a compound of General Formula I:

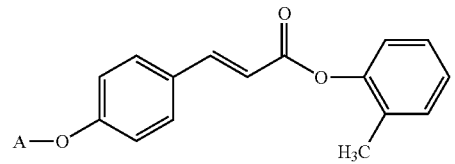

(where —OA is an alkoxy group) that exhibits an ultraviolet A wave absorptive capacity which increases over time and that has an ultraviolet B wave absorptive capacity.

5 Claims, 7 Drawing Sheets

ULTRAVIOLET ABSORBER

TECHNICAL FIELD

The present invention relates to an ultraviolet absorber for inhibiting ultraviolet rays.

BACKGROUND ART

Sunlight is divided into the ultraviolet ray, the visible ray and the infrared ray according to wavelength. Among them, the ultraviolet ray has beneficial aspects such as generating vitamin D in human bodies, and accordingly sunbathing has been recommended for a long period. However, accompanied by the destruction of the ozone layer in the stratosphere, the amount of ultraviolet rays reaching the earth surface has increased and a health damage caused by ultraviolet rays has become perceived as a problem. As the health damage, there are acute health damages such as sunburn and chronic health damages such as an increased risk of diseases, e.g., a skin cancer as a result of the accumulation of the damage over a long period. Thus, there is regarded as necessary a countermeasure that effectively blocks ultraviolet rays harmful to human bodies.

The ultraviolet ray is divided into three types, namely, UVA having a large wavelength (320 to 400 nm), UVB having a medium wavelength (280 to 320 nm) and UVC having a short wavelength (200 to 280 nm). However, UVC and a part of UVB (of 290 nm or less in wavelength) are absorbed in the ozone layer, and therefore they hardly reach the earth surface. The ratio of the ultraviolet rays in sunlight reaching the earth surface is around 6%, and of these ultraviolet rays, UVA accounts for around 90 to 95% and UVB for the rest. UVA penetrates deeply into the dermis and is regarded as a cause of wrinkles and sagging skin. In addition, UVA mutates melanin in the epidermis, resulting in darkened skin (suntan). On the other hand, UVB causes inflammation in the skin (sunburn) in a short period and a pigmentation after few days.

In order to prevent health damages caused by the exposure to ultraviolet rays, there are cosmetics generally used (for example, sunscreen creams) in which a component for preventing ultraviolet rays is blended. As the component preventing ultraviolet rays blended in such a type of cosmetics, there are organic ultraviolet absorbers that absorb ultraviolet rays and inorganic ultraviolet scattering agents that reduce the amount of ultraviolet rays reaching the skin by reflecting and scattering them. In many cases, these cosmetics are made up of a combination of multiple ultraviolet absorbers and ultraviolet scattering agents, making use of their characteristics.

The ultraviolet absorbers have their own absorbance wavelengths defined by the chemical structure of the substances and, as UVB absorbers, p-methoxycinnamic acid-2-ethylhexyl is widely used (see Patent Document 1). On the other hand, there are only few ultraviolet protective cosmetics commercially available at the present which contain an organic ultraviolet absorber with high absorptive capacities in the UVA wavelength range. In addition, 4-tent-butyl-4-methoxybenzoylmethane (see Patent Document 2) used at the present as a UVA absorber has a UVA absorptive capacity, however, it has poor solubility in solvents used for general cosmetics, which turns out to be a large limitation to the preparation of cosmetics harmless to human bodies.

In addition, as an invention related to a p-alkoxycinnamic acid ester compound, in Patent Document 3, there is disclosed a thermosensitive recording material characterized in that its thermosensitive color developing layer contains at least one type of the cinnamic acid ester compounds of the following General Formula:

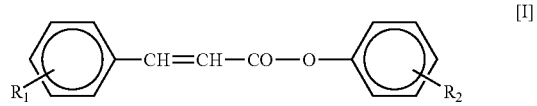

(where $R_1$ is an alkyl group, an aralkyl group, an alkoxy group, a cyclohexyl group or a halogen atom; and $R_2$ is an alkyl group, an aralkyl group, an alkoxy group, an acyl group, a cyclohexyl group, a hydrogen atom or a halogen atom), and there is described a p-methoxycinnamic acid p-ethylphenyl ester as a specific example of the cinnamic acid ester compounds. However, in Patent Document 3, there is not indicated that the described cinnamic acid ester compound is used as an ultraviolet absorber.

Further, Patent Document 4 discloses an ultraviolet absorber characterized by containing a diphenyl unsaturated compound, and as the diphenyl unsaturated compound, the compound (claim 3) of the following General Formula:

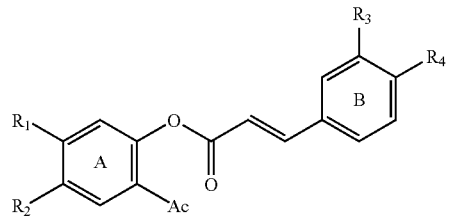

(where $R_1$, $R_2$, $R_3$ and $R_4$ are H or an alkoxyl group) is exemplified. An important aspect to be noted here is that the diphenyl unsaturated compound of the General Formula is a compound in which one of the two phenyl groups (A) has an Ac (acetyl group).

[Patent Document 1]
Japanese Patent Application Publication No. JP-A-2001-49233

[Patent Document 2]
Japanese Patent Application Publication No. JP-A-2004-51567

[Patent Document 3]
Japanese Patent Application Publication No. JP-A-3-297685

[Patent Document 4]
Japanese Patent Application Publication No. JP-A-7-26247

DISCLOSURE OF THE INVENTION

[Problems to be Solved by the Invention]

However, the above general-purpose ultraviolet absorber (p-methoxycinnamic acid-2-ethylhexyl) in the related art does not have a sufficient absorptive capacity in the UVA range. In addition, sunscreen cosmetics containing the general-purpose ultraviolet absorber have an ultraviolet absorptive capacity which does not significantly increase over the course of ultraviolet irradiation time. Therefore, such sunscreen cosmetics do not satisfactorily meet the requirement of the users for a sustained ultraviolet absorptive capacity, because the cosmetics need to be re-applied on sunburned skin frequently at regular time intervals. In addition, it has been confirmed that the ultraviolet absorber 4-tert-butyl-4-methoxy-benzoylmethane, which absorbs UVA, has an ultraviolet absorptive capacity that decreases over the course of ultraviolet irradiation time. Due to this confirmed fact and its poor solubility as mentioned above, 4-tert-butyl-4-methoxy-benzoylmethane is not necessarily suitable for practical applications such as cosmetics.

In order to solve the problems described above, it is an object of the present invention to provide a novel ultraviolet absorber with a high ultraviolet A wave absorptive capacity that contains, as an active ingredient, an ultraviolet absorbing compound that has: a strong absorptive capacity in the UVA range; an ultraviolet absorptive capacity that does not decrease over the course of ultraviolet irradiation time; and an excellent solubility. In addition, it is another object of the present invention to provide a method for using an ultraviolet absorber capable of being used in an application requiring a sustained ultraviolet ray-A absorptive effect, and to provide a cosmetic composition, a coating composition and an organic polymer composition that contain the ultraviolet absorber. Further, it is yet another object of the present invention to provide an ultraviolet absorbing compound that is an active ingredient of the ultraviolet absorber.

[Means for Solving the Problems]

The present invention relates to: according to a first aspect, an ultraviolet absorber including, as an active ingredient, a compound of General Formula 1:

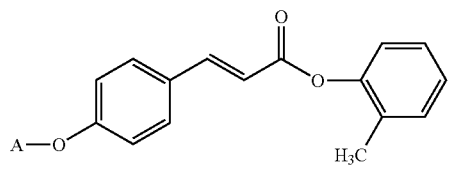

(where —OA is an alkoxy group) that exhibits an ultraviolet A wave absorptive capacity which increases over time and that has an ultraviolet B wave absorptive capacity;

according to a second aspect, the ultraviolet absorber according to the first aspect in which the —OA is a methoxy group;

according to a third aspect, the ultraviolet absorber according to the first aspect in which the —OA is an ethoxy group;

according to a fourth aspect, a method of use of an ultraviolet absorber, characterized in that the ultraviolet absorber according to any one of the first to third aspects is applied to a material whose usage requires a sustained ultraviolet A absorptive effect;

according to a fifth aspect, the method of use according to the fourth aspect in which the material is a cosmetic composition;

according to a sixth aspect, the method of use according to the fourth aspect in which the material is a coating composition;

according to a seventh aspect, the method of use according to the fourth aspect in which the material is an organic polymer susceptible to ultraviolet degradation;

according to an eighth aspect, a cosmetic composition, characterized by containing the ultraviolet absorber as described in any one of the first to third aspects;

according to a ninth aspect, a coating composition, characterized by including the ultraviolet absorber as described in any one of the first to third aspects;

according to a tenth aspect, an organic polymer composition, characterized by including the ultraviolet absorber as described in any one of the first to third aspects; and according to an eleventh aspect, a compound of General Formula I:

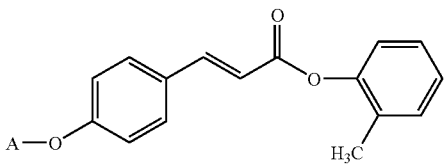

(where —OA is a methoxy group or an ethoxy group).

[Effects of the Invention]

Accordingly, the present invention can provide an ultraviolet absorber that: has a strong absorptive capacity in the UVA range and an absorptive capacity in the UVB range to have an ultraviolet inhibitory effect in a wide range of wavelength; has characteristics not found in the related art that an ultraviolet absorptive capacity increases over the course of ultraviolet irradiation time in both the UVA and the UVB ranges; and has an excellent solubility. In addition, usage of the ultraviolet absorber according to the present invention can provide extremely effective ultraviolet inhibition in various fields of application. Such fields of application include cosmetics and various preparations such as quasi-drugs that are directly applied to human skin for blocking ultraviolet rays and of which a sustained ultraviolet A absorptive effect is required; and materials that need to absorb or block ultraviolet rays, for example, woven clothes, nonwoven clothes, plastic products such as plastic films and plastic sheets, rubber products and coatings. In other words, a method for using an ultraviolet absorber possessing such effects and advantages is developed. In addition, the present invention can provide a composition containing an ultraviolet absorber extremely advantageous to and useful for products for these applications. Further, the present invention can provide an ultraviolet absorbing compound that is an active ingredient of such ultraviolet absorbers.

For example, when the ultraviolet absorber of the present invention is used as a component in sunscreen cosmetics, its ultraviolet inhibitory effect is maintained over a long period of time at a high level without frequently re-applying the cosmetics as in the case of the related art, because the ultraviolet absorber of the present invention has an ultraviolet absorptive capacity that increases over the course of ultraviolet irradiation time. Ultraviolet inhibitory effect of ultraviolet absorbers in the related art, on the other hand, lowers or does not enhance over the course of ultraviolet irradiation time, and therefore it has been common to frequently re-apply the sunscreen cosmetics that include such ultraviolet absorbers.

In addition, when the ultraviolet absorber of the present invention is applied to a coating composition, coatings made of the coating composition inhibit absorption of harmful ultraviolet rays over a long period of time, and the coating films obtain enhanced long-term weatherability and safety. The reason for this is that the ultraviolet absorber has an ultraviolet inhibitory effect over a wide range of wavelength spectrum, and also has a characteristic that its ultraviolet absorptive capacity is increased by ultraviolet-ray irradiation. The ultraviolet absorber can be effectively utilized also as a stabilizer for organic polymers by being kneaded in the organic polymers or being applied to the surface of the polymers.

BEST MODES FOR CARRYING OUT THE INVENTION

Figure 1:
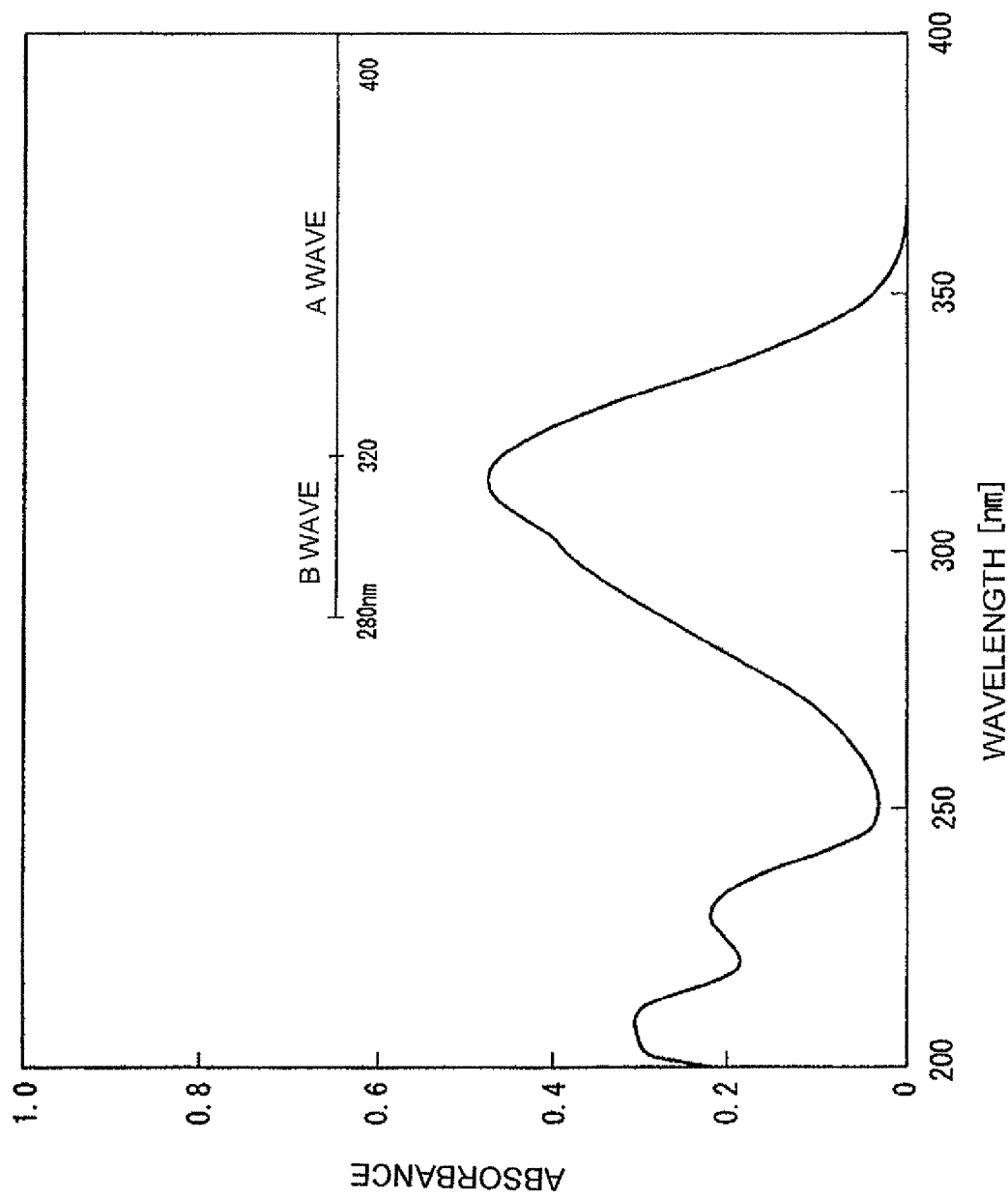
FIG. 1 is a figure showing an ultraviolet absorption spectrum of an O-tolyl-4-methoxycinnamate compound obtained in Example 1.

The ultraviolet absorber of the present invention will be further described in detail.

The ultraviolet absorber of the present invention is characterized by containing the compound of General Formula I as an active ingredient. Specific examples of the compound include O-tolyl-4-methoxycinnamate in which —OA in General Formula I is a methoxy group and O-tolyl-4-ethoxycinnamate in which —OA in General Formula I is an ethoxy group.

In addition, the ultraviolet absorber of the present invention can be used with a combination of ultraviolet absorbing compounds in the related art, along with the compound of General Formula I. Specific examples of the ultraviolet absorbing compound in the related-art include: a mixture of 2-(4-(2-hydroxy-3-dodecyloxy-propyl)oxy-2-hydroxyphenyl)-4,6-(bis(2,4-dimethylphenyl))-1,3,5-triazine and 2-(4-(2-hydroxy-3-tridecyloxy-propyl)oxy-2-hydroxyphenyl)-4,6-(bis(2,4-dimethylphenyl))-1,3,5-triazine (trade name: TINUVIN 400; manufactured by Ciba Specialty Chemicals Corp.); 2-(4-(octyl-2-methylethanoate) oxy-2-hydroxyphenyl)-4,6-(bis(2,4-dimethylphenyl))-1,3,5-triazine (trade name: TINUVIN 479; manufactured by Ciba Specialty Chemicals Corp.), tris(2,4,6-(2-{4-(octyl-2-methylethanoate)oxy-2-hydroxyphenyl})-1,3,5-triazine (trade name: TINUVIN 777; manufactured by Ciba Specialty Chemicals Corp.), 2-hydroxybenzophenone, 5-chloro-2-hydroxybenzophenone, 2,4-dihydroxybenzophenone, 2-hydroxy-4-methoxybenzophenone, 2-hydroxy-4-octyloxybenzophenone, 4-dodecyloxy-2-hydroxybenzophenone, 2-hydroxy-4-octadecyloxybenzophenone, 2,2'-dihydroxy-4-methoxybenzophenone, 2,2'-dihydroxy-4,4'-dimethoxybenzophenone, phenylsalicylate, p-tert-butylphenylsalicylate, p-(1,1,3,3-tetramethylbutyl) phenylsalicylate, 3-hydroxyphenylbenzoate, phenylene-1,3-dibenzoate, 2-(2-hydroxy-5'-methylphenyl) benzotriazole, 2-(2-hydroxy-5-tert-butylphenyl)-5-chloro benzotriazole, 2-(2-hydroxy-3,5-di-tert-butylphenyl) benzotriazole, 2-(2-hydroxy-5-tert-butylphenyl)benzotriazole, 2-(2-hydroxy-4-octylphenyl) benzotriazole, and 2-(2'-hydroxy-5'-methaeryloxyethylphenyl)-2H-1-benzotriazole. These ultraviolet absorbing compounds can be used individually or in a combination of two or more types thereof. In addition, the ultraviolet absorber of the present invention has a particularly strong ultraviolet A absorptive capacity. Therefore, ultraviolet rays in a wide range of wavelength range can be inhibited by combining the ultraviolet absorber of the present invention with an ultraviolet absorber that has a strong ultraviolet B absorptive capacity.

The ultraviolet absorber of the present invention can be used in any material and for any purposes of usage so long as the material is required to possess a sustained ultraviolet A absorptive effect. The ultraviolet absorber can be blended in, for example, skin external preparations such as cosmetic compositions, coatings, dyes, pigments, various resins, synthetic rubbers, latexes, films, and fibers. The blending amount thereof can be determined according to the ultraviolet absorptive capacity that is aimed at.

When the ultraviolet absorber of the present invention is blended in a cosmetic composition, the form of the cosmetic composition is not particularly limited so long as the effect of the present invention can be exhibited. Examples thereof include a sunscreen cosmetic composition in the product form of an ointment, a cream, an emulsion, a lotion, etc. In a cosmetic composition, the ultraviolet absorber of the present invention can be used in combination with various components generally used in cosmetic compositions such as pigments, oil solutions, surfactants, fluorine compounds, resins, gums, antiseptics, perfumes, humectants, salts, solvents, antioxidants, chelating agents, neutralizers, pH adjusters, insect repellents, polymerization initiators, plasticizers, physiologically active components, catalysts and thickeners. When the ultraviolet absorber of the present invention is blended in a cosmetic composition, the blending amount thereof can be determined according to the ultraviolet absorptive capacity that is aimed at, however, is usually 0.001 to 30% by mass, preferably 0.01 to 10% by mass, based on the total mass of the composition.

In addition, for the purpose of preventing deteriorations in quality, coloring, deteriorations in freshness, etc., of foods and the like caused by ultraviolet rays, the ultraviolet absorber of the present invention can be used in wrapping materials for foods and the like, for example a resin film made of polyethylene, polypropylene, polyvinyl chloride, nylon, polyester, polyvinylalcohol and the like, by being added to, dispersed in or applied onto the wrapping materials.

In addition, the ultraviolet absorber of the present invention can be used in a coating composition as an additive for preventing the deterioration caused by ultraviolet rays and enhancing weatherability. The blending amount thereof is preferably in a range of 1 to 30% by mass, based on the total mass of the coating composition. In addition, the ultraviolet absorber of the present invention can be used in combination with other additives used in coating compositions in the related art. Solvents used in this case are not particularly limited and an appropriate organic solvent can be selected from such perspectives as enhancing workability in applying the coating compositions, homogeneity and smoothness of the coating, and the adhesion of the coating to the base material.

EXAMPLES

Example 1

Synthesis of an O-tolyl-4-metlioxycinnamate compound

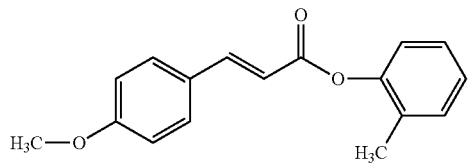

(Synthesis)

16.67 g of O-cresol (0.154 mol, 1.1 equivalents) was added to and dissolved in 28 mL of dimethylformamide and thereto, 16.25 g (0.161 mol, 1.15 equivalents) of triethylamine was added. Next, while maintaining the resultant reaction mixture at 40° C. or less, 27.6 g (0.140 mol, 1 equivalent) of 4-methoxycinnamoyl chloride (synthesized by reacting 4-methoxycinnamic acid and thionyl chloride according to the standard method) was gradually added to the reaction mixture to effect the reaction. After the completion of the reaction, the reaction mixture was warmed to 50 to 60° C. and thereto, 34 mL of water was gradually added to cool down the reaction mixture to 10° C. or less. A crystal was obtained by filtering the reaction mixture and was washed by sprinkling isopropyl alcohol over the crystal. Then, 31.6 g of a crude product was obtained by reduced pressure-drying of the crystal. Next, the crude product was recrystallized in isopropyl alcohol to obtain 30.2 g of white colored O-tolyl-4-methoxycinnamate (yield: 80.23%).

(Physical property values and spectrum data)

Melting point: 93 to 94° C.

Spectrum data:

IR ($\nu$ cm$^{-1}$) (KBr method): 1713, 1628, 1600, 1510, 1448, 1464, 1335, 1327, 1312, 1260, 1220, 1175, 1146, 1110, 1030, 839, 745, 532.

$^1$H-NMR (300 MHz/CDCl$_3$) δ ppm: 2.20 (s, 3H, Ph—CH$_3$), 3.85 (s, 3H, Ph—OCH$_3$), 6.53 (d, 1H, J=16 Hz, Ph—CH=CH-COO), 7.84 (d, 1H, J=16 Hz, Ph—CH=CH—COO), 6.7 to 7.7 (m, 8H, Ar)

The ultraviolet-ray absorption spectrum of the compound obtained in Example 1 was measured and the result shown in FIG. 1 was obtained.

Example 2

Synthesis of an O-tolyl-4-ethoxycinnamate compound

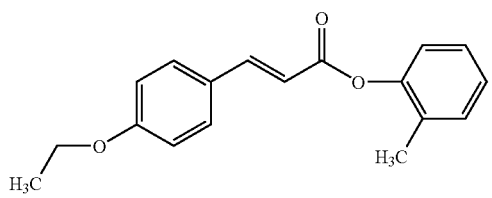

(Synthesis)

To 14.75 mL of dimethylformamide, 8.16 g of O-cresol (0.075 mol, 1.1 equivalents) and 7.86 g (0.078 mol, 1.15 equivalents) of triethylamine were added. Next, while maintaining the resultant reaction mixture at 40 to 45° C., 14.3 g (0.0676 mol, 1 equivalent) of 4-ethoxycinnamoyl chloride (synthesized by reacting 4-ethoxycinnamic acid and thionyl chloride according to the standard method) was gradually added to the reaction mixture to effect the reaction. After the completion of the reaction, the reaction mixture was warmed to 50 to 60° C. and thereto, 36 mL of methanol was gradually added to cool down the reaction mixture to 10° C. or less. A crystal was obtained by filtering the reaction mixture and was washed by sprinkling isopropyl alcohol over the crystal. Then, 16.4 g of a crude product was obtained by reduced pressure-drying of the crystal. Next, the crude product was recrystallized in isopropyl alcohol to obtain 13.2 g of white colored O-tolyl-4-ethoxycinnamate (yield: 69.1%).

(Physical property values and spectrum data)

Melting point: 108 to 109° C.

Spectrum data:

IR ($\nu$ cm$^{-1}$) (KBr method): 1719, 1629, 1601, 1512, 1489, 1471, 1326, 1312, 1260, 1221, 1207, 1174, 1145, 1042, 999, 838, 751

$^1$H-NMR (300 MHz/CDCl$_3$) δ ppm: 1.44 (t, 3H, J=6.6 Hz, CH$_3$, CH$_2$O), 2.22(s, 3H, Ph—CH$_3$), 4.09 (q, 2H, J=6.6 Hz, CH$_3$CH$_2$O), 6.52 (d, 1H, J=16 Hz, Ph—CH=CH—COO), 7.83 (d, 1H, J=16 Hz, Ph—CH=CH—COO), 6.7 to 7.7 (m, 8H, Ar)

Figure 2:
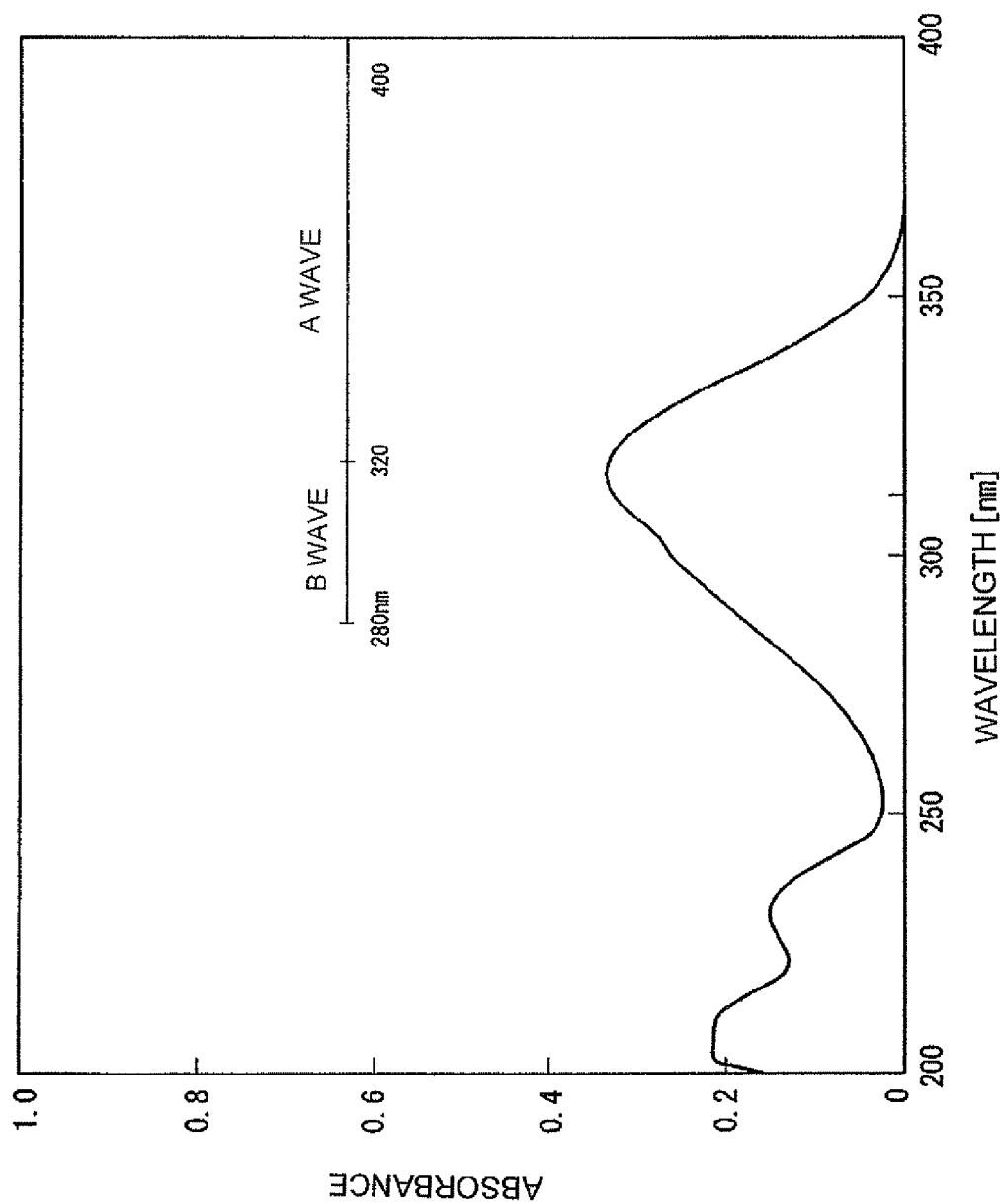
FIG. 2 is a figure showing an ultraviolet absorption spectrum of an O-tolyl-4-ethoxycinnamate compound obtained in Example 2.

The ultraviolet-ray absorption spectrum of the compound obtained in Example 2 was measured to obtain the result shown in FIG. 2.

Reference Example 1

4-methoxycinnamic acid-2-ethylhexyl (manufactured by Wako Pure Chemical Industries, Ltd.)

Figure 3:
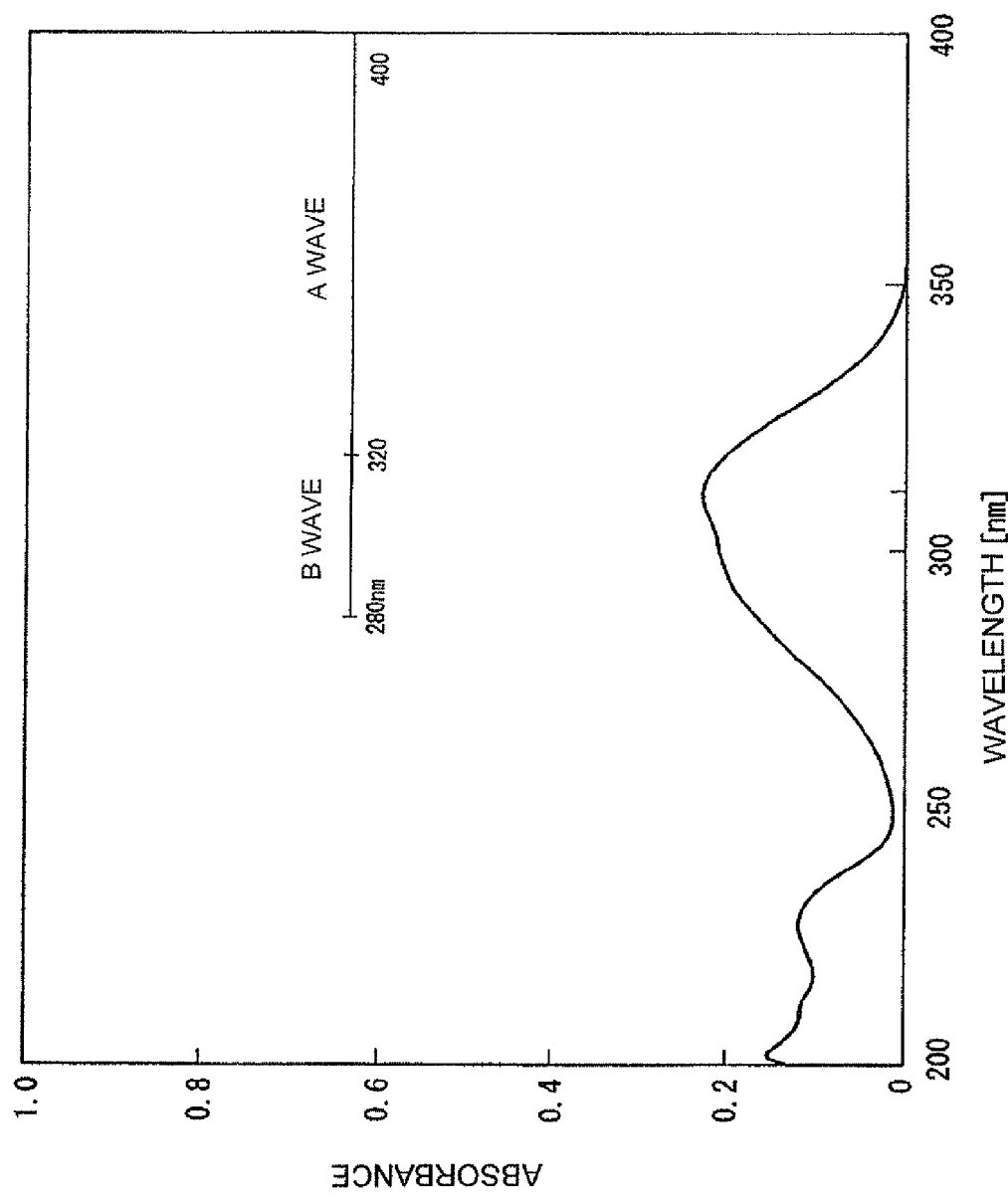
FIG. 3 is a figure showing an ultraviolet absorption spectrum of 4-methoxycinnamic acid-2-ethylhexyl of Reference Example 1.
Figure 4:
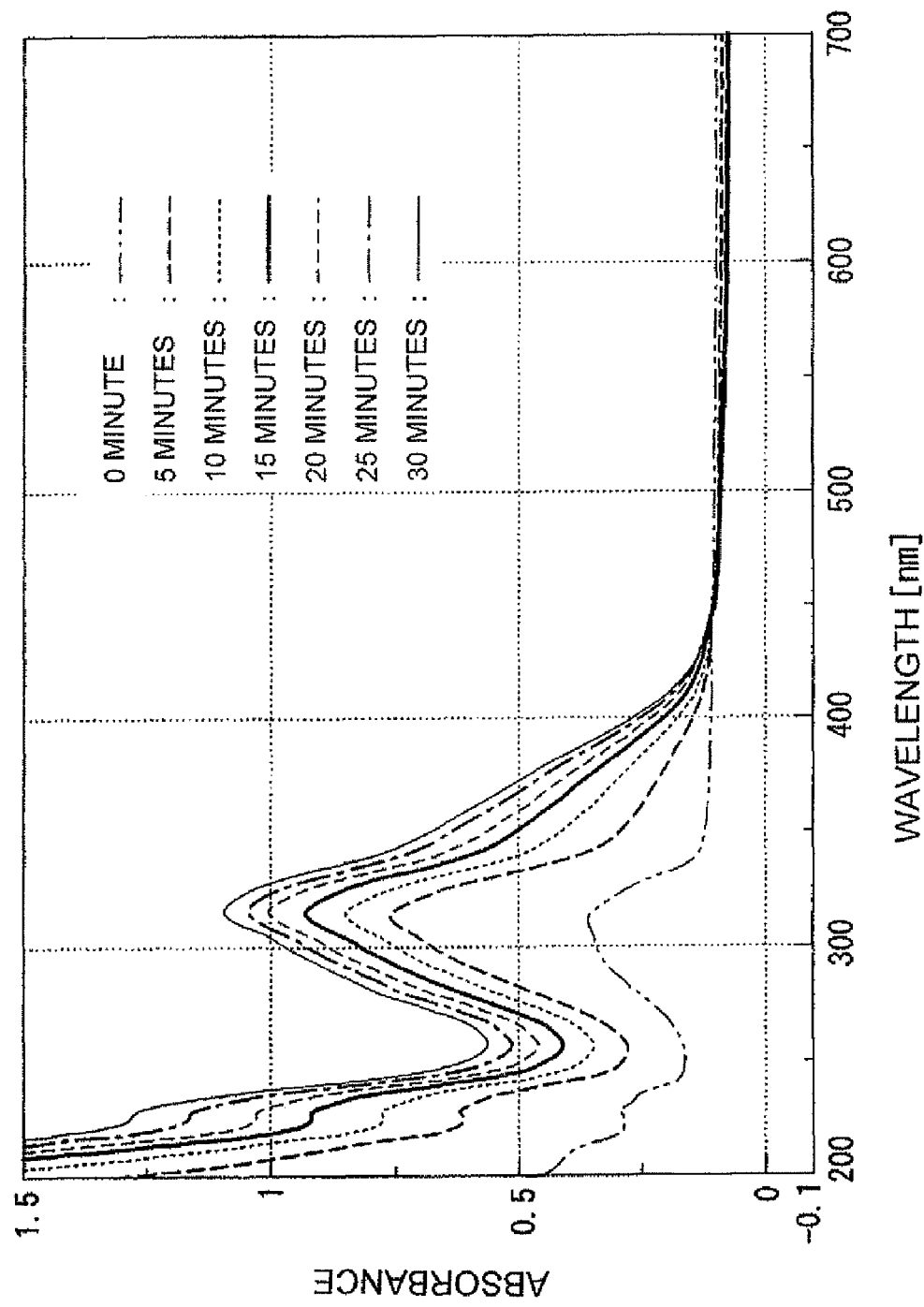
FIG. 4 is a figure showing ultraviolet absorption spectra of the compound of Example 1 measured for different ultraviolet irradiation times.
Figure 5:
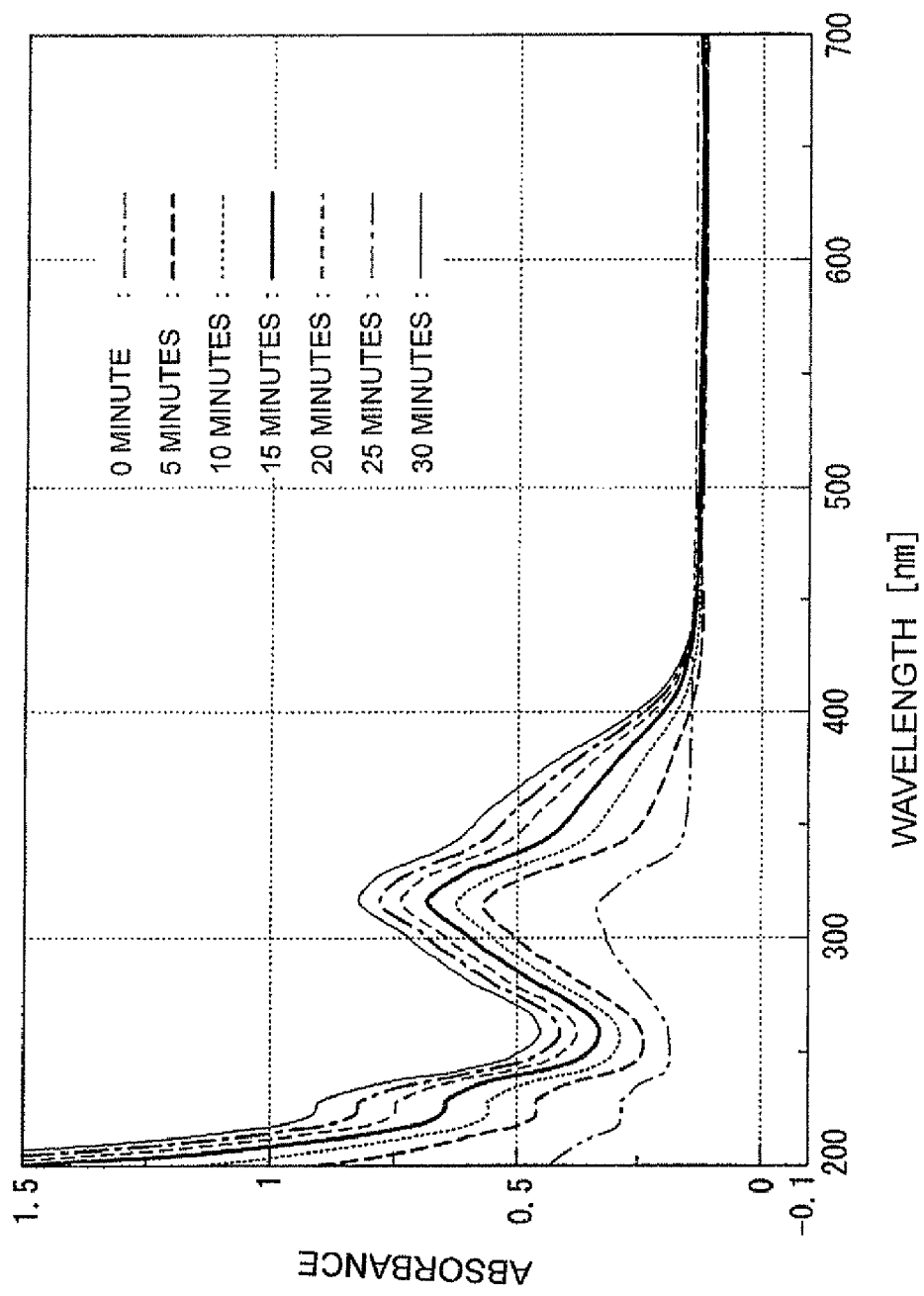
FIG. 5 is a figure showing ultraviolet absorption spectra of the compound of Example 2 measured for different ultraviolet irradiation times.
Figure 6:
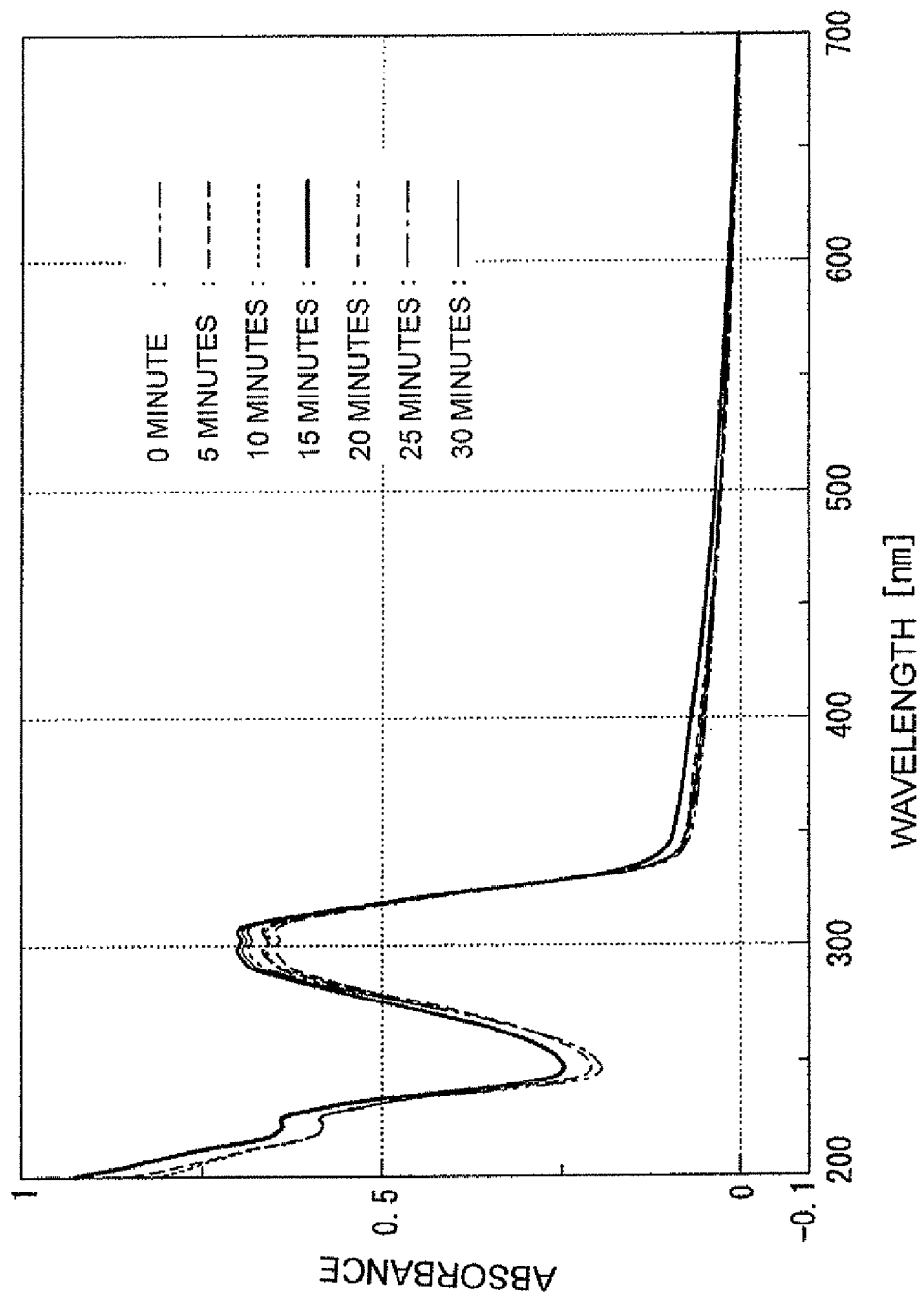
FIG. 6 is a figure showing ultraviolet absorption spectra of the compound of Reference Example 1 measured for different ultraviolet irradiation times.
Figure 7:
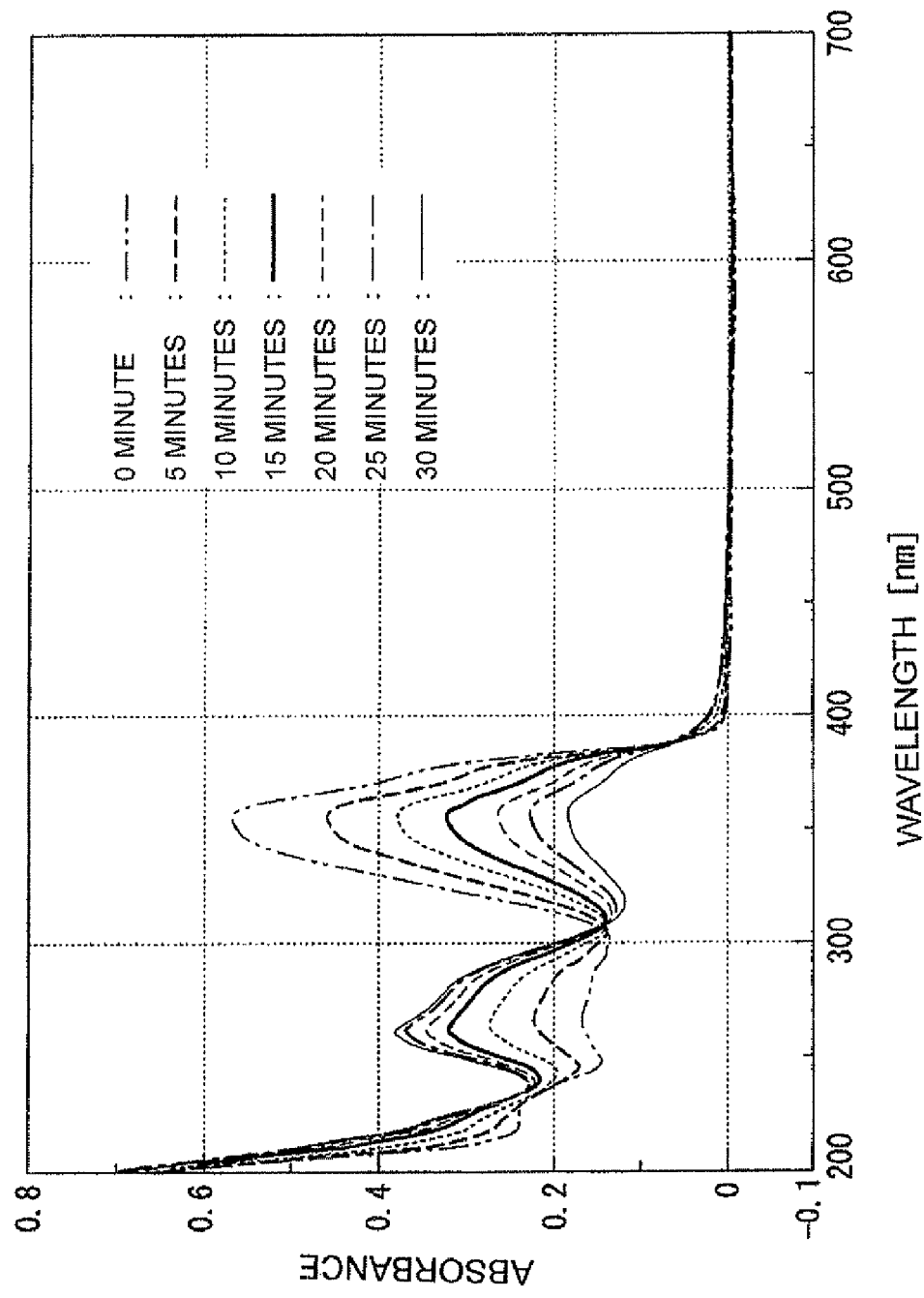
FIG. 7 is a figure showing ultraviolet absorption spectra of the compound of Reference Example 2 measured for different ultraviolet irradiation times.

The ultraviolet-ray absorption spectrum of Reference Example 1 was measured to obtain the result shown in FIG. 3.

Reference Example 2

4-tert-butyl-4'-methoxy-dibenzoylmethane (manufactured by Wako Pure Chemical Industries, Ltd.)

Comparison of the ultraviolet absorption spectra of the compounds of the present invention shown in FIG. 1 and FIG. 2 with the ultraviolet absorption spectrum of a UVB absorbing compound in the related art shown in FIG. 3 revealed that the compounds of the present invention have their maximum absorption in a range of wavelength longer than that of the UVB absorbing compound in the related art, and have many absorption bands in the UVA range. Therefore, it was shown that the compounds of the present invention have an excellent ultraviolet absorbing effect in the UVA range. The compounds of the present invention had an absorptive capacity also in the UVB range. Therefore, it was shown that the compounds of the present invention have an ultraviolet inhibitory effect over a wide range of wavelength.

Test Example 1

Ultraviolet Inhibiting Effects (Sample)

Using ointment base (manufactured by Sankyo Co., Ltd.; plastibase), ointment base alone (Sample A), an ointment containing the compound of Example 1 in a content of 5% (Sample B), an ointment containing the compound of Example 2 in a content of 5% (Sample C), an ointment containing the compound of Reference Example 1 in a content of 5% (Sample D), and an ointment containing the compound of Reference Example 2 in a content of 5% (Sample E) were prepared.

(Test Method)

The abdomen of a 5-6 week-old, Hartley-type male guinea pig was dehaired with an electric hair clipper and further shaved with an electric shaver on the previous day of the test date. Pentobarbital Na (30 mg/Kg) was administered to the abdominal cavity of the guinea pig to anesthetize and 100 mg of ointment or of each sample was flatting-applied to the abdomen of the guinea pig in a band-shape of 1.5 cm in width and 6 or 7 cm in length. Five minutes after the application, the skin in the applied part was covered by felt which had six (3×2) round-shaped holes of 1 cm in diameter each and the skin covered was irradiated (using an ultraviolet-ray erythema generating apparatus (trade name: TK-151; manufactured by UNICOM Co., Ltd.)) with ultraviolet rays of 3,000 Lux for 90 seconds. Inhibiting effects were evaluated by scoring the strength of the round-shaped erythema generated 24 hours after the irradiation. The result thereof is shown in Table 2. The score for three positions to which the sample was applied is 12 points, when perfect inhibition was observed. Scores: 0 (not inhibited at all); 1 (slightly inhibited); 2 (apparently inhibited); 3 (substantially inhibited); 4 (perfectly inhibited).

TABLE 1

| Ultraviolet inhibiting scores | |
| --- | --- |
| Sample | Ultraviolet inhibiting score |
| Sample A | 0 |
| Sample B | 10 |
| Sample C | 11 |
| Sample D | 11 |
| Sample E | 9 |

As shown in Table 1, it was confirmed that the ointment containing the compound of Example 1 in a content of 5% and the ointment containing the compound of Example 2 in a content of 5% have ultraviolet inhibiting effects at the same level as or a higher level than those of the ointment containing the compound of Reference Example 1 in a content of 5% and the ointment containing the compound of Reference Example 2 in a content of 5%, used as positive controls.

Test Example 2

Solubility Test (Sample)

Sample a: the O-tolyl-4-methoxycinnamate compound synthesized in Example 1

Sample b: the Compound of Reference Example 2

(Measurement)

The amounts of various organic solvents capable of dissolving 100 mg of each sample at room temperature (23 to 25° C.) were measured. For dissolving the sample, a 50 mL polypropylene conical tube (manufactured by CORNING Inc.) was used, and dissolution was carried out by stirring with a shaker (trade name: Vortex G-56; manufactured by Scientific Ind. Inc.) for 1 minute.

(Result)

The amounts (mL) (concentration) of solvent required to dissolve 100 mg of each sample are shown in Table 2.

TABLE 2

| Solvent | Sample a | Sample b |
| --- | --- | --- |
| Ethanol | 10 (1) | 17.5 (0.57) |
| Methanol | 7.5 (1.3) | 12.5 (0.8) |
| Ether | 3 (3.3) | 1 (10) |
| Acetone | 1> (>10) | 1> (>10) |
| Ethyl acetate | 1> (>10) | 1> (>10) |
| Isopropyl alcohol | 15 (0.67) | 20 (0.5) |
| N-methylpyrrolidone | 1> (>10) | 1> (>10) |

From this result, it is apparent that the compound of Example 1 has better solubility than that of the compound of Reference Example 2 in almost all the organic solvents.

Test Example 3

Ultraviolet Irradiation Test (Sample)

Ointments (samples B, C, D and E) prepared in Test Example 1 were interposed between two pieces of synthetic quartz plates to prepare measurement samples.

(Test Method)

From a light radiated from a 500 W ultra-high pressure mercury vapor lamp (trade name: USH-500D; manufactured by Ushio Inc.), the visible light was removed through a water filter of 5 cm and an ultraviolet transmitting and visible light-absorbing filter (trade name: UV-D33S; manufactured by AGC Techno Glass Co., Ltd.). Then, each measurement sample was irradiated with ultraviolet rays mostly in the UVA and the UVB ranges. Ultraviolet rays irradiation time was set at 0, 5, 10, 15, 20, 25 and 30 minutes. The results of the test are shown in the ultraviolet absorption spectra of FIG. 4 to FIG. 7.

(Result)

With respect to the samples B and C, as irradiation time became longer, their absorption strength in the UVB range increased, and the samples began to absorb lights in the UVA range while showing an increasing absorption strength over time. Although the sample D has an absorptive capacity in the UVB range, its absorption strength did not substantially vary over the course of ultraviolet irradiation time. With respect to the sample E, as ultraviolet irradiation time became longer, its absorption strength in the UVB range increased to some degrees, but its absorption strength in the UVA range decreased substantially.

From the above results, it was confirmed that the compounds of Reference Example 1 and Reference Example 2 have absorption strength that decreases or remains the same under ultraviolet irradiation in the expected ultraviolet range, that is, in the UVA and the UVB ranges, showing no improvement in ultraviolet absorptive capacity. On the other hand, the compounds of Example 1 and Example 2 have a characteristic different from those of many other ultraviolet absorbers that their ultraviolet absorptive capacity increases further by the ultraviolet irradiation in the UVA and the UVB ranges. Therefore, these compounds are strongly expected to become ultraviolet absorbers covering the UVA and the UVB ranges.

Examples 3 and 4, Comparative Example 1

Cosmetic Compositions

Components 1 to 11 in the following Table 3 were homogeneously mixed to prepare a mixture (a). Then, components 12 to 15 were homogeneously mixed and then was added to the mixture (a) and emulsifying-mixed to prepare a sunscreen emulsion.

TABLE 3

| No. | Component | Example 3 | Example 4 | Comparative Example 1 |
|---|---|---|---|---|
| 1 | O-tolyl-4-methoxycinnamate (Example 1) | 20 | | |
| 2 | O-tolyl-4-ethoxycinnamate (Example 2) | | 20 | |
| 3 | 4-methoxycinnamic acid-2-ethylhexyl (Reference Example 1) | | | 10 |
| 4 | 4-tert-butyl-4'-methoxy-dibenzoylmethane (Reference Example 2) | | | 10 |
| 5 | Decamethylcyclopentasiloxane | 15 | 15 | 15 |
| 6 | Trimethylsiloxysilicic acid | 5 | 5 | 5 |
| 7 | Lauryl PEG-9 polydimethylsiloxyethyldimethicone | 1.5 | 1.5 | 1.5 |
| 8 | Octamethylcyclotetrasiloxane | 8.5 | 8.5 | 8.5 |
| 9 | Isononyl isononanoate | 5 | 5 | 5 |
| 10 | Silicone-hydrophobized titanium dioxide | 5 | 5 | 5 |
| 11 | Silicone-hydrophobized zinc oxide | 8 | 8 | 8 |
| 12 | Purified water | 25 | 25 | 25 |
| 13 | Phenoxyethanol | 0.5 | 0.5 | 0.5 |
| 14 | 1,3-butylene glycol | 3 | 3 | 3 |
| 15 | Ethanol | 3.5 | 3.5 | 3.5 |

Example 5 to Example 8

Cosmetic Compositions

In addition, according to the following blending examples, cosmetic compositions were prepared.

Example 5

| | % by mass |
|---|---|
| Cyclomethicone | 5.0 |
| Zinc oxide | 9.0 |
| Dimethicone | 3.5 |
| Glycerin | 5.0 |
| Ethanol | 5.0 |
| O-tolyl-4-methoxycinnamate (Example 1) | 3.0 |
| Perfluorohexylethyldimethylbutyl | 6.0 |
| Squalane | 2.0 |
| Dimethicone-copolyol | 3.0 |
| Titanium oxide | 3.0 |
| Ceramide 2 | 2.5 |
| Water | Balance |
| Total | 100.0 |

Example 6

| | % by mass |
|---|---|
| Octylsilylated titanium oxide | 1.0 |
| Zinc oxide | 3.0 |
| Sorbitan isostearate | 1.0 |
| Trifluoroalkyldimethyltrimethylsiloxysilicic acid | 3.0 |
| Perfluoroalkyldimethicone-copolyol | 2.0 |
| Methyltrimethicone | 5.0 |
| Cyclomethicone | 10.0 |
| Dimethicone | 20.0 |
| O-tolyl-4-methoxycinnamate (Example 1) | 2.0 |
| Ethanol | 5.0 |
| Paraben | 0.1 |
| Water | Balance |
| Total | 100.0 |

Example 7

| | % by mass |
|---|---|
| Cyclomethicone | 25.0 |
| Dimethicone | 1.0 |
| O-tolyl-4-ethoxycinnamate (Example 2) | 5.0 |
| Trimethylsiloxycinnamic acid | 5.0 |
| Glutathione | 1.0 |
| BG (1,3-butylene glycol) | 5.0 |
| Isostearic acid | 1.0 |
| Zinc oxide | 5.0 |
| Titanium oxide | 2.0 |
| Polybutylene glycol/PPG-9/1 copolymer | 1.0 |
| Dimethicone copolyol | 0.5 |
| Water | Balance |
| Total | 100.0 |

Example 8

| | % by mass |
|---|---|
| Cyclomethicone | 15.0 |
| Methicone | 5.0 |
| Zinc oxide | 7.0 |
| O-tolyl-4-methoxycinnamate (Example 1) | 3.0 |
| O-tolyl-4-ethoxycinnamate (Example 2) | 3.0 |
| BG (1,3-butylene glycol) | 3.0 |
| Methyl polymethacrylate | 1.0 |
| Oxybenzone-3 | 5.0 |
| Trimethylsiloxysilicic acid | 5.0 |
| Dimethicone-copolyol | 3.0 |
| Octyl palmitate | 2.0 |
| Denatured alcohol | 2.5 |
| Water | Balance |
| Total | 100.0 |

Test Example 4

Ultraviolet absorbing effects of the sunscreen emulsions obtained in Example 3 to Example 8 and Comparative Example 1 were evaluated.

(Test Method)

The abdomen of a 5-6 week-old Hartley-type male guinea pig was dehaired with an electric hair clipper and further shaved with an electric shaver on the previous day of the test date. Pentobarbital Na (30 mg/Kg) was administered to the abdominal cavity of the guinea pig to anesthetize and 100 mg of ointment or of each sample was flatting-applied to the abdomen of the guinea pig in a band-shape of 1.5 cm in width and 6 or 7 cm in length. Five minutes after the application, the skin in the applied part was covered by felt which had six (3×2) round-shaped holes of 1 cm in diameter each and the skin covered was irradiated (using an ultraviolet-ray erythema generating apparatus (trade name: TK-151; manufactured by UNICOM Co., Ltd.)) with ultraviolet rays of 3,000 Lux. Inhibiting effects were evaluated by scoring the strength of the round-shaped erythema generated, immediately after the ultraviolet irradiation to the sunscreen emulsion, or after the ultraviolet irradiation for 30 minutes, 1 hour or 2 hours. The results thereof are shown in Table 4. The score for three positions to which the sample was applied is 12 points, when perfect inhibition was observed.

Scores: 0 (not inhibited at all); 1 (slightly inhibited); 2 (apparently inhibited); 3 (almost perfectly inhibited); 4 (perfectly inhibited).

TABLE 4

Ultraviolet inhibiting scores according to irradiation time

| Sample | 0 minute | After UV irradiation for 30 minutes | After UV irradiation for 1 hour | After UV irradiation fro 2 hours |
|---|---|---|---|---|
| Sunscreen emulsion of Example 3 | 12 | 11 | 12 | 12 |
| Sunscreen emulsion of Example 4 | 12 | 12 | 12 | 11 |
| Sunscreen emulsion of Example 5 | 12 | 11 | 12 | 12 |
| Sunscreen emulsion of Example 6 | 11 | 12 | 11 | 11 |
| Sunscreen emulsion of Example 7 | 12 | 12 | 12 | 11 |
| Sunscreen emulsion of Example 8 | 11 | 11 | 12 | 12 |
| Sunscreen emulsion of Comparative Example 1 | 12 | 11 | 9 | 8 |

The ultraviolet inhibiting scores of the sunscreen emulsions of Example 3 to Example 8 demonstrated an excellent ultraviolet inhibiting effect of the sunscreen emulsions that remained almost the same even in the progression of ultraviolet irradiation time. On the contrary, with respect to the sunscreen emulsion of Comparative Example 1, the longer the ultraviolet irradiation time, the lower the ultraviolet inhibiting scores became.

From the above results, it was found that while the sunscreen emulsion of Comparative Example 1 has an ultraviolet absorptive capacity that lowers over the course of ultraviolet irradiation time, the sunscreen emulsions of Example 3 to Example 8 have an ultraviolet absorptive capacity that does not lower even after a long period of time of irradiation and that is maintained at a high level over time in the UVA and the UVB ranges.

Examples 9 and 10 and Comparative Examples 2 and 3

Coating Compositions

Coating compositions were prepared in the blending ratios shown in the following Table 5 and were spray-coated on a polycarbonate resin plate of 3 mm in thickness (trade name: Lexan LS-2; manufactured by General Electric Company) so that the coating film after curing becomes 8 μm in thickness. The component of organic solvents was evaporated by subjecting the coating film to heating treatment in an oven at 80° C. for 3 minutes, and the coating film was irradiated with 3,000 mJ/cm$^2$ of integrated amount of light at 340 nm to 380 nm in wavelength (the value measured by an ultraviolet-ray actinometer (trade name: UV-351 (SN type); manufactured by Orc Manufacturing Co., Ltd.)), using a high pressure mercury vapor lamp in air to obtain a cured coating film.

TABLE 5

| Component | Example 9 | Example 10 | Comparative Example 2 | Comparative Example 3 |
|---|---|---|---|---|
| Dipentaerythritol hexaacrylate | 9.4 | 9.4 | 9.4 | 9.4 |
| Urethane acrylate | 7.5 | 7.5 | 7.5 | 7.5 |
| Tris(2-acryloyloxy-ethyl) isocyanurate | 10.0 | 10.0 | 10.0 | 10.0 |
| Benzophenone | 0.9 | 0.9 | 0.9 | 0.9 |
| Compound of Example 1 | 3.1 | | | |
| Compound of Example 2 | | 3.1 | | |
| Compound of Comparative Example 1 | | | 3.1 | |
| Compound of Comparative Example 2 | | | | 3.1 |
| Bis(2,2,6,6-tetramethyl-4-piperidyl) sebacate | 0.3 | 0.3 | 0.3 | 0.3 |
| Isobutanol | 15.6 | 15.6 | 15.6 | 15.6 |
| n-butyl acetate | 18.8 | 18.8 | 18.8 | 18.8 |
| Propylene glycol monomethyl ether | 21.9 | 21.9 | 21.9 | 21.9 |
| Methyl isobutyl ketone | 12.5 | 12.5 | 12.5 | 12.5 |
| Weatherability | A | A | B | B |

Test Example 5

Weatherability Test of Coating Compositions

Using a sunshine carbon arc lamp-mode accelerating weatherability testing machine (according to JIS K-5400 (1990) 9.8.1), the test plate on which a coating film was formed was subjected to the treatment for 3,000 hours to visually measure the state of the coating film. The test piece was taken out of the testing machine to inspect floating, peel or the like of the coating film. Weatherability was evaluated in the following manner: the test piece in which floating, peel or the like had not been caused was evaluated as "A"; the test piece in which a floating of 0.5 mm or less in width from the slit had been detected was evaluated as "B"; and the test piece in which a floating of 0.5 mm or more in width from the slit had been detected was evaluated as "C". The results of the evaluation are shown in Table 5.

From the above results, it was found that the ultraviolet absorber of the present invention is useful for enhancing weatherability of a coating composition.

Industrial Applicability

The present invention is useful in a field ranging from livingware to industrial products where an ultraviolet absorber is utilized. Examples include cosmetics and various preparations such as quasi-drugs that are directly applied to human skin for blocking ultraviolet rays, and woven cloths, nonwoven cloths, plastic products such as plastic films or sheets, rubber products, and coatings, etc., that require absorption or blocking ultraviolet-rays.

The invention claimed is:

1. A cosmetic composition comprising:
an ultraviolet absorber; and
at least one member selected from the group consisting of oil solutions, surfactants, fluorine compounds, gums, antiseptics, perfumes, salts, antioxidants, chelating agents, neutralizers, pH adjusters, polymerization initiators, and catalysts,
wherein the ultraviolet absorber comprises, as an active ingredient, a compound of General Formula I:

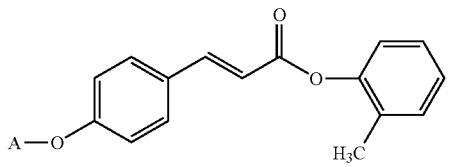

(where —OA is an alkoxy group) that exhibits an ultraviolet A wave absorptive capacity which increases over time and that has an ultraviolet B wave absorptive capacity.

2. The ultraviolet absorber according to claim 1, wherein the —OA is a methoxy group.

3. The ultraviolet absorber according to claim 1, wherein the —OA is an ethoxy group.

4. The cosmetic composition according to claim 1, wherein the ultraviolet absorber is present in an amount between 0.001 to 30% by mass, based on a total mass of the cosmetic composition.

5. The cosmetic composition according to claim 1, wherein the ultraviolet absorber is present in an amount between 0.01 to 10% by mass, based on a total mass of the cosmetic composition.

* * * * *